(12) United States Patent
Bäck et al.

(10) Patent No.: US 11,051,997 B2
(45) Date of Patent: Jul. 6, 2021

(54) DISPOSABLE PANT-TYPE ABSORBENT ARTICLE

(71) Applicant: Essity Hygiene and Health Aktiebolag, Gothenburg (SE)

(72) Inventors: Lucas Bäck, Gothenburg (SE); Anna Klinte Olsson, Gothenburg (SE); Katarina Eriksson, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 16/496,672

(22) PCT Filed: Mar. 28, 2017

(86) PCT No.: PCT/SE2017/050295
§ 371 (c)(1),
(2) Date: Sep. 23, 2019

(87) PCT Pub. No.: WO2018/182469
PCT Pub. Date: Oct. 4, 2018

(65) Prior Publication Data
US 2020/0306104 A1     Oct. 1, 2020

(51) Int. Cl.
*A61F 13/15* (2006.01)
*A61F 13/491* (2006.01)
*A61F 13/496* (2006.01)

(52) U.S. Cl.
CPC .... *A61F 13/4915* (2013.01); *A61F 13/15699* (2013.01); *A61F 13/496* (2013.01)

(58) Field of Classification Search
CPC ............ A61F 13/4915; A61F 13/15699; A61F 13/496

USPC .... 604/349, 385.03, 385.24, 385.25, 385.29, 604/385.3, 387, 392, 396, 394
See application file for complete search history.

(56) References Cited

U.S. PATENT DOCUMENTS 5,562,650 A * 10/1996 Everett ............. A61F 13/15203
                                                      604/378
2003/0023224 A1* 1/2003 Ishikawa ........... A61F 13/49019
                                                      604/385.24
(Continued)

FOREIGN PATENT DOCUMENTS

CN     101394819 A     3/2009
CN     103402476 A     11/2013
(Continued)

OTHER PUBLICATIONS

International Search Report and Written Opinion for International Application No. PCT/SE2017/050295, dated Dec. 12, 2017—13 pages.
(Continued)

*Primary Examiner* — Jacqueline F Stephens
(74) *Attorney, Agent, or Firm* — Buchanan Ingersoll & Rooney P.C.

(57) ABSTRACT

A disposable pant-type absorbent article, such as a pant diaper, a sanitary pant or incontinence pant is described. The disposable pant-type absorbent article has a longitudinal direction (Y) and a transverse direction (X). The disposable pant-type absorbent article is adapted for a male user. A method for manufacturing such a disposable pant-type absorbent article is also described.

24 Claims, 7 Drawing Sheets

(56) References Cited

U.S. PATENT DOCUMENTS

| | | | |
|---|---|---|---|
| 2004/0243083 A1* | 12/2004 | Matsuda | A61F 13/496 604/385.01 |
| 2007/0208317 A1 | 9/2007 | Krautkramer et al. | |
| 2010/0108554 A1 | 5/2010 | Melius et al. | |
| 2013/0041340 A1 | 2/2013 | Kawakami et al. | |
| 2013/0079743 A1 | 3/2013 | Mukai et al. | |
| 2013/0010298 A1 | 4/2013 | Mukai et al. | |
| 2016/0166444 A1 | 6/2016 | Finlayson et al. | |

FOREIGN PATENT DOCUMENTS

| | | |
|---|---|---|
| CN | 105636563 A | 6/2016 |
| JP | 2006-181172 A | 7/2006 |
| JP | 2010-179028 A | 8/2010 |
| JP | 2013-013580 A | 1/2013 |
| JP | 2016-202569 A | 12/2016 |
| WO | 03059223 A1 | 7/2003 |
| WO | 2011070737 A1 | 6/2011 |
| WO | 2011/132687 A1 | 10/2011 |
| WO | 2012117710 A1 | 9/2012 |
| WO | 2013/005423 A1 | 1/2013 |
| WO | 2014098683 A1 | 6/2014 |
| WO | 2016099362 A1 | 6/2016 |
| WO | 2017044022 A1 | 3/2017 |
| WO | 2017058069 A1 | 4/2017 |
| WO | 2018106160 A1 | 6/2018 |

OTHER PUBLICATIONS

Office Action (Notification of the Second Office Action) dated Apr. 1, 2020, by the State Intellectual Property Office (SIPO) of the People's Republic of China in corresponding Chinese Patent Application No. 201780087486.9, and an English Translation of the Office Action. (22 pages).

Office Action (Notification of the Third Office Action) dated Aug. 21, 2020 by the China National Intellectual Property Administration (CNIPA) of the People's Republic of China in corresponding Chinese Patent Application No. 201780087486.9 and an English Translation of the Office Action. (25 pages).

Extended European Search Report dated Sep. 22, 2020, issued by the European Patent Office in corresponding European Application No. 17904296.5-1102, (8 pages).

Office Action (Notice of Reasons for Rejection) dated Dec. 14, 2020, by the Japanese Patent Office in corresponding Japanese Patent Application No. 2019-552155, and an English Translation of the Office Action. (11 pages).

Office Action (Decision of Rejection) dated Jan. 6, 2021 by the China National Intellectual Property Administration (CNIPA) of the People's Republic of China in corresponding Chinese Patent Application No. 201780087486.9, and an English Translation of the Office Action. (22 pages).

* cited by examiner

DISPOSABLE PANT-TYPE ABSORBENT ARTICLE

CROSS REFERENCE TO RELATED APPLICATIONS

This is a U.S. National Phase application of PCT/SE2017/050295, filed Mar. 28, 2017, the disclosure of which is incorporated herein by reference in its entirety for all purposes.

TECHNICAL FIELD

The disclosure relates to a disposable pant-type absorbent article, such as a pant diaper, a sanitary pant or incontinence pant, having a longitudinal direction and a transverse direction, wherein said disposable pant-type absorbent article is adapted for a male user. The disclosure further relates to a method of production of a disposable pant-type absorbent article.

BACKGROUND

In the field of disposable pant-type absorbent articles there is a general desire to provide absorbent articles with increased comfort and fit as well as discrete underwear-like visual appearance. Due to anatomical differences between men and women it is not always suitable to have only one kind of absorbent articles. Thus, further improvement in terms of comfort, fit and discrete underwear-like visual appearance is desirable.

SUMMARY

It is an object of the present disclosure to provide a disposable pant-type absorbent article being adapted for a male user addressing the above mentioned desires. This object is achieved at least partly by the features of the independent claims. Variations of the disclosure are found in the dependent claims.

The disclosure relates to a disposable pant-type absorbent article, such as a pant diaper, a sanitary pant or incontinence pant, having a longitudinal direction and a transverse direction. The disposable pant-type absorbent article is adapted for a male user and comprises a front panel made of laminated web material having a waist edge, a pair of leg edges and a pair of side edges. The article further comprises a back panel having a waist edge, a pair of leg edges, and a pair of side edges. An absorbent insert is located mainly in a crotch portion of the absorbent article and is connected to the front and back panels and having an absorbent core with longitudinal core edges, a front core edge and a back core edge. The core has a front segment with a length in the longitudinal direction which is 30% of the total length of the core in the longitudinal direction and extending from a front core edge, a back segment with a length in the longitudinal direction which is 30% of the total length of core in the longitudinal direction and extending from a back core edge, and a middle segment with a length in the longitudinal direction which is 40% of the total length of core in the longitudinal direction and being located between the front and back segments. The core has a wide portion in the front segment, which wide portion has a width in the transverse direction that is at least 1.1 times greater than the maximal width in the transverse direction of the core in the back segment. The laminated web material of the front panel has a first at least partly elastic region extending primarily in the transverse direction and being located adjacent the leg edges of the front panel, and a second at least partly elastic region extending primarily in the transverse direction and being located next to the first elastic region and closer to the waist edge of the front panel. The first at least partly elastic region is distinct from the second at least partly elastic region in terms of at least one structural elastic feature. An elasticised part of the laminated web material of the first at least partly elastic region, or an inner imaginary extension of an elasticised part of the laminated web material of the first at least partly elastic region, meet a longitudinal core edge in said wide portion of the core.

One advantage with the disclosure is that a product according to the above is anatomically adapted for male users. Due to the anatomy of male genitalia, the location of urine discharge for male users is positioned more towards the front of the absorbent product compared with female users, and also not as certain as it is for female users. Urine discharge for male users can occur over a much greater area than for a female user depending on the orientation of the penis. Also, the orientation of the penis may shift during use of the absorbent product due to movement of the male user. The wide portion of the front segment ensures that the core is wider in a part of the absorbent article where likelihood of urine discharge is greatest. This increases the likelihood that the urine discharge will be absorbed by the core and will not fall outside of the core.

The structural elastic feature may be that an elasticised part of the laminated web material of the first at least partly elastic region has a higher tensile stress at a given elongation in the transverse direction than an elasticised part of the laminated web material of the second at least partly elastic region.

Additionally, the higher tensile stress of the elasticised part of the first at least partly elastic region of the laminated web material, either meeting a longitudinal core edge directly in the wide portion or that an inner imaginary extension of an elasticised part of the first at least partly elastic region meets a longitudinal core edge in the wide portion ensures that the leg edges of the absorbent article contracts to provide a tight fit against the legs of the user while at the same time ensuring that the wide portion of the core is extended in an essentially transverse direction. This further reduces the risk of leakage from the absorbent article.

Alternatively, or in combination, the structural elastic feature making the first at least partly elastic region distinct from the second at least partly elastic region may be the spacing between neighbouring elastic threads. The resulting contracting strength of an elastic region is typically a function of the spacing between neighbouring elastic threads, wherein smaller spacing results in increased tensile stress.

Alternatively, or in combination, the structural elastic feature making the first at least partly elastic region distinct from the second at least partly elastic region may be the mass density of the elastic threads. Elastic threads with high mass density typically results in increased tensile stress.

Alternatively, or in combination, the structural elastic feature making the first at least partly elastic region distinct from the second at least partly elastic region may be the level of elongation of the elastic threads with the front panel in a flat and un-gathered state. Elastic threads that have been applied and fastened to the elastic laminate of the front panel with a high level of elongation compared with the length of the thread in a natural state typically results in increased tensile stress of the elastic laminate.

The front segment of the core may have an area which is at least 1.1 times greater, specifically at least 1.2 times greater, and more specifically at least 1.3 times greater than the area of the back segment. One advantage with having a larger area of the front segment of the core than the area of the back segment of the core is that the core will have a greater area where the likelihood of urine discharge is the greatest. This further increases the likelihood that the urine discharge will be absorbed by the core and will not fall outside of the core.

The wide portion may have a length in the longitudinal direction in the range of 30-200 millimetres, specifically 40-180 millimetres, and more specifically 50-160 millimetres. The length is adapted to fit the majority of variations of male anatomy.

The wide portion may have a length in the longitudinal direction in the range of 20-130%, specifically 25-120%, and more specifically 30-100% of the length of the front portion of the core. The length is adapted to fit the majority of variations of male anatomy.

The wide portion may have a width in the transverse direction that is at least 1.2 times greater, specifically at least 1.3 times greater, than the maximal width in the transverse direction of the core in the back segment. A greater width increases the likelihood of urine discharge falling within the wide portion of the core.

An elasticised part of the laminated web material of the first at least partly elastic region may extend from an outer end adjacent the side edge of the front panel to an inner end located spaced apart from the core, and the inner imaginary extension of an elasticised part of the laminated web material of the first at least partly elastic region may extend linearly from the inner end of a linear portion of an elasticised part of the laminated web material of the first at least partly elastic region, or tangentially from the inner end of a curved portion of an elasticised part of the laminated web material of the first at least partly elastic region.

The wide portion of the core may extend a distance corresponding to at least 20% of the length of the front segment of the core below a position where an elasticised part of the laminated web material of the first at least partly elastic region, or an inner imaginary extension of an elasticised part of the laminated web material of the first at least partly elastic region, meet a longitudinal core edge. This assists in shaping the wide portion such that the likelihood of urine discharge will be absorbed by the core and will not fall outside of the core.

The wide portion of the core may extend a distance corresponding to at least 20% of the length of the front segment of the core above a position where an elasticised part of the laminated web material of the first at least partly elastic region, or an inner imaginary extension of an elasticised part of the laminated web material of the first at least partly elastic region, meet a longitudinal core edge. This further assists in shaping the wide portion such that the likelihood of urine discharge will be absorbed by the core and will not fall outside of the core.

A width of the core adjacent the front core edge in the transverse direction may be smaller than the width of the core in the transverse direction in the rest of the front segment of the core. This further assists in shaping the wide portion such that the likelihood of urine discharge will be absorbed by the core and will not fall outside of the core.

The width of the core adjacent the front core edge in the transverse direction may be equal to the width of at least part of the core in the back segment of the core in the transverse direction. This simplifies production of the core and reduces waste during production of the core.

An elasticised part of the laminated web material of the second at least partly elastic region may extend over an area of the front segment of the absorbent core that extends from the front core edge in the longitudinal direction by less than or equal to 30 mm, specifically less than or equal to 20 mm, such that the front core edge is pressed towards a user during use of the absorbent article. This further assists in shaping the wide portion such that the likelihood of urine discharge will be absorbed by the core and will not fall outside of the core.

The absorbent article may comprise a front segment configured for receiving the genitals of a male user, wherein elasticised parts of the laminated web material of the first at least partly elastic region extends on transverse sides of the front segment but not completely over the front segment for enabling the absorbent core in the front segment to bulge outwardly during use of the article. The absorbent article further comprises at least one elongated side elastic element attached in a substantially longitudinal direction on each transverse side of the front segment for providing a side gathering effect along the transverse sides of the front segment, such that the absorbent core within the front segment, under the influence of the side elastic elements is adapted to bulge outwardly during use of the article to form an internal pocket for receiving the genitals of a male user. This configuration of the elastic parts and side elastic elements provide a "cup" or bulge shape of the absorbent insert and/or core in order for the male genitalia to fit inside the "cup" or bulge shape. This further assists in shaping the wide portion such that the likelihood of urine discharge will be absorbed by the core and will not fall outside of the core.

The elasticised part of the laminated web material of the first and/or second at least partly elastic region may end before the longitudinal core edges.

The elasticised part of the laminated web material of the first at least partly elastic region may overlap the longitudinal core edges of the absorbent core.

The front and back panels may be made of individual parts that are mutually interconnected by means of the absorbent insert, and where the front panel may have a length in the longitudinal direction of between 110-400 mm.

The first at least partly elastic region may have a length in the longitudinal direction of 5-30 mm, specifically 9-25 mm or more specifically 10-20 mm.

The ratio of the fluid absorbent capacity of a front half of the absorbent core and a back half of the absorbent core may be at least 55/45, specifically at least 60/40. As the discharge of fluid more likely is greater in the front half than in the back half, the distribution of the fluid absorbent capacity reflects this in order to provide a sufficient absorbent capacity where it is most needed.

The maximal width of the absorbent core may be between 120-200 mm in the transverse direction and the minimal width of the absorbent core may be 60 mm, more specifically 80 mm in the transverse direction. These measurements are adapted to fit the majority of male user's anatomy.

The laminated web material of the front panel may have a third at least partly elastic region extending primarily in the transverse direction, being located adjacent the waist edge.

The absorbent core may comprise pulp fibres and superabsorbent particles.

The area of the absorbent insert located outside of the absorbent core may be substantially free from pulp fibres and superabsorbent particles.

The disclosure further relates to a method for manufacturing a disposable pant-type absorbent article such as a pant diaper, a sanitary pant or incontinence pant, having a longitudinal direction and a transverse direction, where the disposable pant-type absorbent article is adapted for a male user. The article comprises a front panel made of laminated web material and having a waist edge, a pair of leg edges and a pair of side edges and a back panel having a waist edge, a pair of leg edges, and a pair of side edges. An absorbent insert is located mainly in a crotch portion of the absorbent article and is connected to the front and back panels and has an absorbent core. The core has a front segment with a length in the longitudinal direction which is one-third of the total length of core in the longitudinal direction and extending from a front core edge, a back segment with a length in the longitudinal direction which is one-third of the total length of core in the longitudinal direction and extending from a back core edge, and a middle segment with a length in the longitudinal direction which is one-third of the total length of core in the longitudinal direction and being located between the front and back segments. The method comprises providing the core with a wide portion in the front segment, which wide portion has a width in the transverse direction that is at least 1.1 times greater than the maximal width in the transverse direction of the core in the back segment, providing the laminated web material of the front panel with a first at least partly elastic region extending primarily in the transverse direction and being located adjacent the leg edges of the front panel, providing the laminated web material of the front panel with a second at least partly elastic region extending primarily in the transverse direction and being located next to the first elastic region and closer to the waist edge of the front panel, providing the first at least partly elastic region with at least one structural elastic feature distinguishing the first at least partly elastic region from the second at least partly elastic region in terms of the at least one structural elastic feature, and arranging the elasticised part of the laminated web material of the first at least partly elastic region, or an inner imaginary extension of the elasticised part of the laminated web material of the first at least partly elastic region, such that it meet a longitudinal core edge in said wide portion of the front segment.

The method displays the same advantages as the article as described above.

DETAILED DESCRIPTION OF PARTICULAR EMBODIMENTS

Various aspects of the disclosure will hereinafter be described in conjunction with the appended drawings to illustrate and not to limit the disclosure, wherein like designations denote like elements, and variations of the described aspects are not restricted to the specifically shown embodiments, but are applicable on other variations of the disclosure. Sizes and distances are not necessarily to scale but may be exaggerated for illustrative purposes.

Figure 1A:
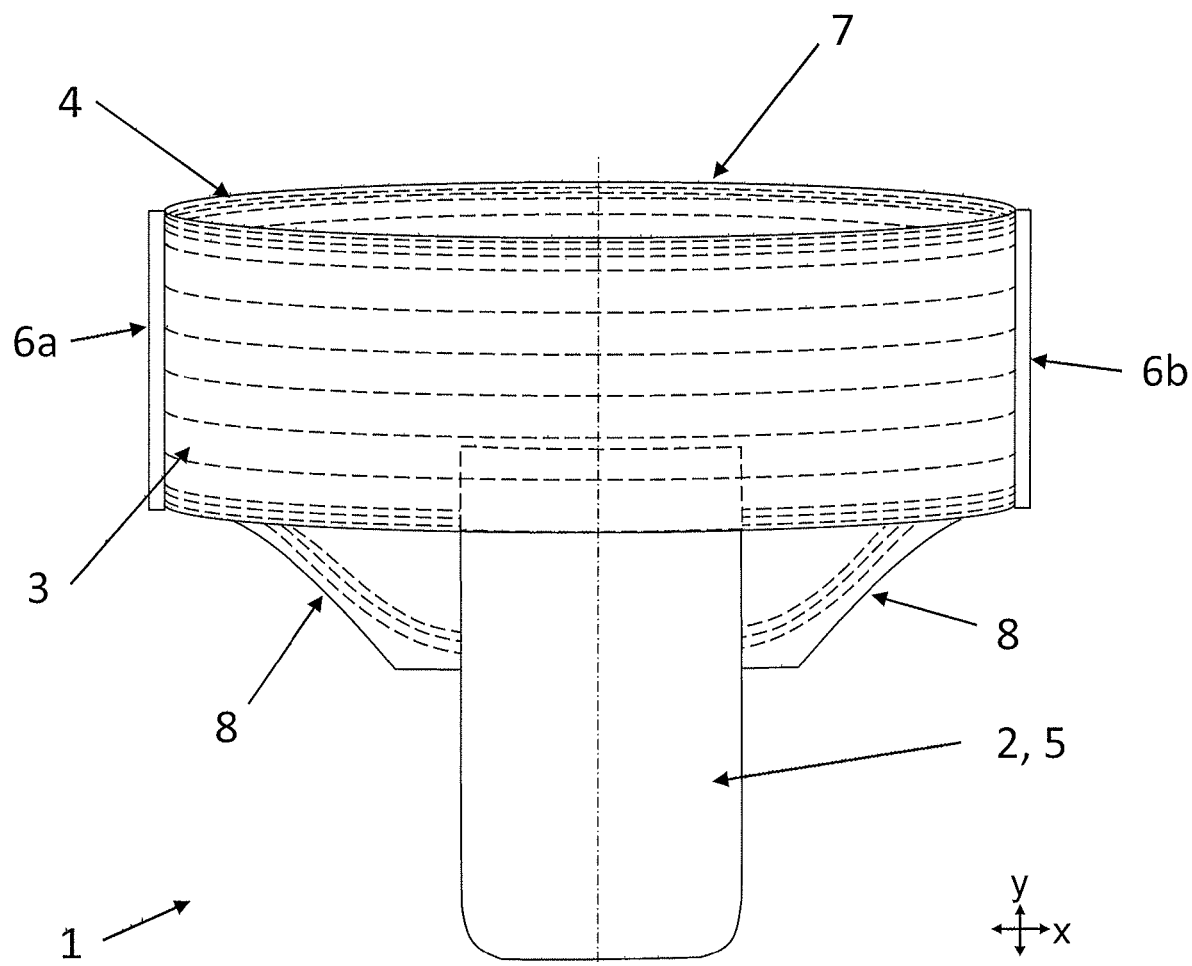
FIG. 1a shows a perspective view of an absorbent article according to the disclosure.

In FIG. 1a of the drawings an example embodiment of a disposable pant-type absorbent article 1 specially adapted for an adult user is schematically illustrated in an assembled and ready-to-use state. The pant-type absorbent article 1 is for example pant diaper, a sanitary pant or an incontinence pant adapted for use of an adult male user. The pant-type absorbent article 1 according to the example embodiment of FIG. 1a comprises a dual-piece chassis having a front panel 3, a back panel 4 and an absorbent insert 2 located mainly in a crotch portion of the absorbent article 1 and connected to interior side of the front and back panels 3, 4 for bridging the gap between the front and back panels 3, 4. The absorbent insert 2 comprises an absorbent core 5 for absorbing body fluid. The absorbent core 5 may be made in one-piece and comprise a single layer, or it may be composed of two or more superposed absorbent layers.

In short, manufacturing of the pant-type absorbent article 1 is performed by first manufacturing two parallel continuous strips of laminated elastic web material that should form the front and back panels 3, 4 of the finished absorbent article 1.

Manufacturing of the laminated elastic web material of the front and back panels 3, 4 are typically performed by feeding a first and a second continuous substantially non-elastic sheet of web material, such as for example a substantially non-elastic nonwoven material, along a machine direction, while simultaneously feeding a plurality of continuous elastic threads arranged parallel with one another. Subsequently, the first and second sheets of web material are joined to each other with a plurality of continuous elastic threads located between the first and second sheets.

The elastic threads are attached to the first and second sheets in a tensioned state and parallel with the web material. Elastic threads arranged parallel with the machine direction, i.e. in the transverse direction X, may for example have adhesive applied thereto before being fastened in a tensioned state to the web material. Alternatively, the web material itself may have adhesive applied to it for securing the elastic threads thereto. The latter is particularly advantageous when the elastic threads exhibit a curved orientation over the transverse length of the absorbent article 1. The finished laminated elastic web will consequently gather when allowing the elastic threads to return to their natural state.

However, while still keeping the elastic threads in tensioned state the method further comprises a step of placing a finished absorbent insert 2 in the gap between the two parallel continuous strips of laminated elastic web, such that the absorbent insert 2 partly overlaps with the both said strips, and subsequently securing the absorbent insert 2 to said strips. The absorbent insert 2 is thus manufactured separately from the front and back panels 3, 4 and subsequently placed and fastened to said panels 3, 4 in a suitable manufacturing step.

The manufacturing method may optionally include the step of providing a flat front and/or flat back design. This would involve having the elastic threads free of adhesive in a central area of the front and/or back panel and performing an interrupting operating of the elastic threads located in the central portion of the front and/or back panel, such that the portion of the elastic threads located in the central portion of the front and/or back panel 3, 4 and are free from adhesive are allowed to return to their natural, un-tensioned, state without exerting a gathering effect on the surrounding web material, thereby creating a flat area at a desired region of the front and/or back panel 3, 4. Such a flat area is typically desirable in the area where the absorbent core 5 overlaps the front and/or back panels 3, 4 because the gathering effect of active elastic threads on the absorbent core 5 may be deemed having a negative effect on the absorption capacity of the absorbent core 5. Alternatively, the elastic means in the second location might have been applied as elastic threads crossing the pant article 1 in the transverse direction that have been deactivated or cut in the area of the core 5. Also the elastic means in the lower area of the front section have also been deactivated similarly. One way of deactivating elastic threads is disclosed in application no PCT/SE2016/051221.

After securing the absorbent insert 2 to the two parallel continuous strips of laminated elastic web the entire continuous material band is folded at a fold line extending substantially in the transverse direction X of the absorbent insert 2, such that the two parallel continuous strips of laminated elastic web becomes superposed after folding. Thereafter the two parallel continuous strips of laminated elastic web are joined to each other at discrete locations at predetermined fixed intervals along the material band using for example ultrasonic welding, to form side seams 6a, 6b of the finished absorbent article 1. Consequently, side edges (not shown) of the front panel 3 are permanently attached to opposite side edges (not shown) of the back panel 4 to form side seams 6a, 6b of the finished and assembled absorbent article 1, thereby also defining a waist-opening 7 and a pair of leg-openings 8.

In a final step the continuous material band is cut in a machine cross direction in the area in or adjacent to the side seams 6a, 6b to transform the folded continuous material band into individual absorbent articles 1. When the laminated elastic web material of the front and back panels 3, 4 is no longer held in stretched state in the transverse direction X the sandwiched elastic threads will cause the web material to gather, i.e. to contract in the transverse direction X and to form small undulations in the laminated elastic web material. An example manufacturing process for such an elastic web material is described more in detail in document WO 2014/098683 A1, which is referred to in its entirety.

Figure 1B:
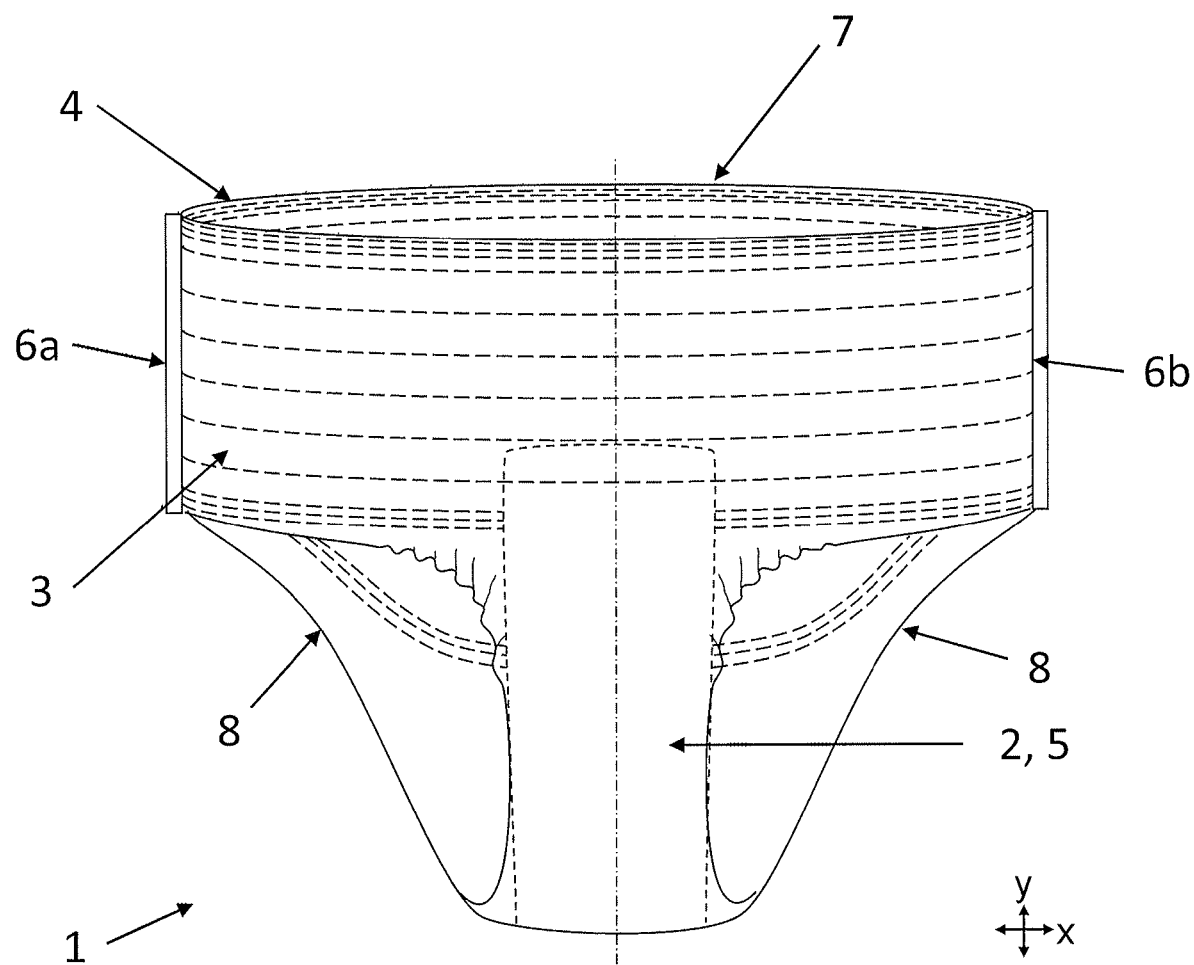
FIG. 1b shows a perspective view of an alternative absorbent article according to the disclosure.

In FIG. 1b of the drawings a second example embodiment of a disposable pant-type absorbent article 1 specially adapted for an adult user is schematically illustrated in an assembled and ready-to-use state. The difference between the articles in FIGS. 1a and 1b is that the article 1 in FIG. 1b comprises a one-piece chassis, i.e. the front and back panels 3, 4 belong to the same single-piece web material that has an integrally formed crotch region interconnecting the front and back panels 3, 4.

Figure 2:
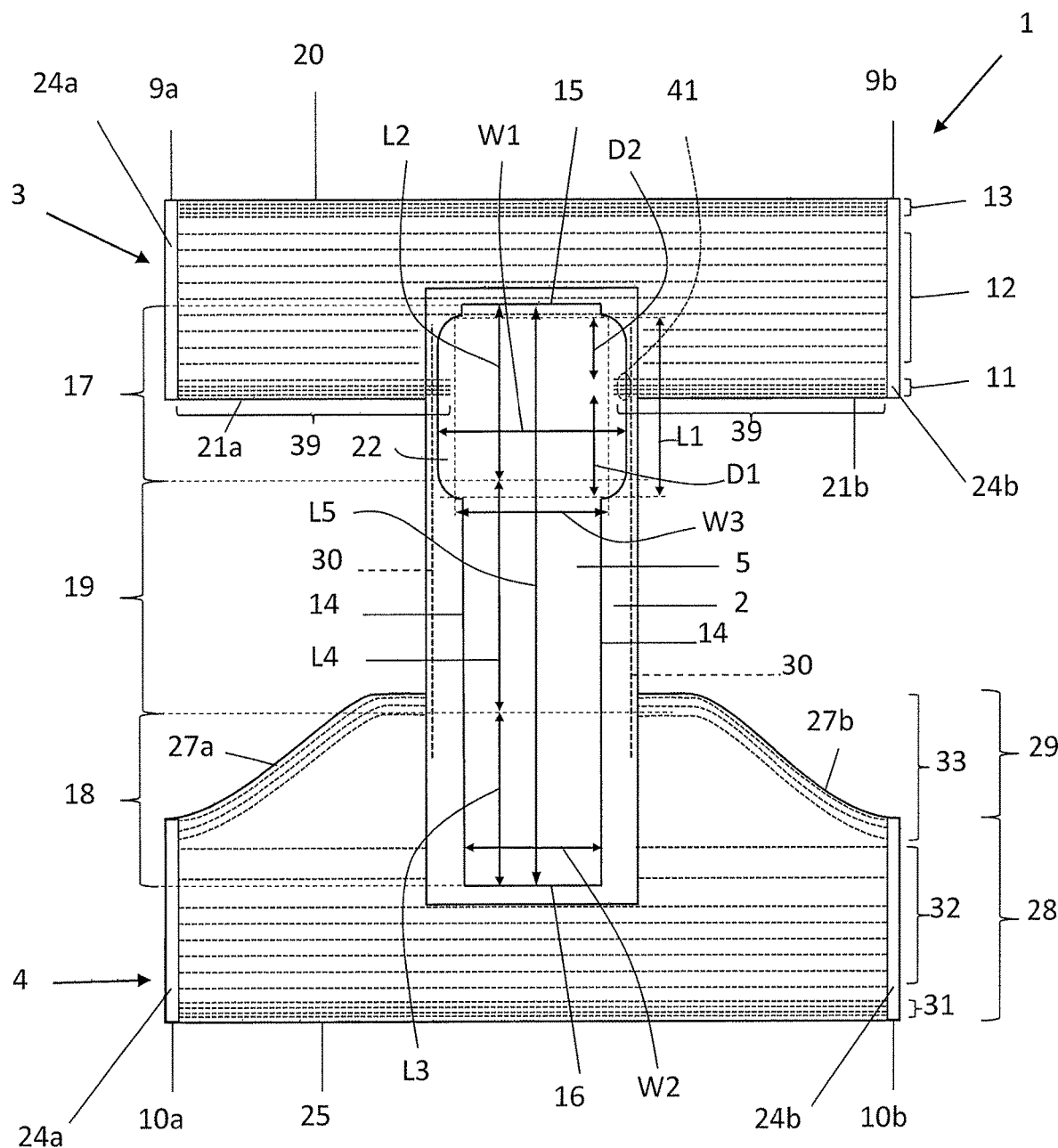
FIG. 2 shows the absorbent article of FIG. 1 in disassembled flat state.

In FIG. 2 of the drawings the same example embodiment of the disposable pant-type absorbent article 1 is schematically illustrated in flat, non-assembled state, and without opposite side edges 9a, 9b, 10a, 10b of the front and back panels 3, 4 being attached to each other in side seams 6a, 6b. This may for example be realised by breaking the side seams 6a, 6b of a finished absorbent article 1 and unfolding the pant-type absorbent article 1 into a flat state. The pant-type absorbent article 1 comprises, in an unfolded and flat state, a longitudinal direction Y that is substantially parallel with a direction of elongation of the absorbent insert 2. The transverse direction X is perpendicular to the longitudinal direction Y.

The pant-type absorbent article 1 of the example embodiment illustrated in FIG. 1 and FIG. 2 comprises a front panel 3 having a waist edge 20, a pair of leg edges 21a, 21b and a pair of side edges 9a, 9b. The front panel 3 has a substantially rectangular shape, and the total length of the front panel 3 in the transverse direction X is typically in the range of about 550-790 mm and the total length of the front panel 3 in the longitudinal direction Y is typically in the range of about 110-400 mm, depending on size of the absorbent article 1. A rectangular shape front panel 3 enables cost-efficient manufacturing because all elastic threads of the front panel 3 may also be arranged in the transverse direction of the absorbent article 1, i.e. along the machine direction in the manufacturing machine. Straight elastic threads require less complex manufacturing equipment and the adhesive for securing the elastic threads may be supplied directly on the elastic threads before laminating the sheets of web material and elastic threads together to form panels. Moreover, the rectangular shaped front panel 3 also enables manufacturing with low level of scrap material caused for example by cutting out complex two-dimensional shapes from a sheet of laminated web material.

The laminated web material of the front panel 3 comprises a first at least partly elastic region 11 extending along the leg edges 21a, 21b of the front panel 3, thereby defining a leg elastic region. The first at least partly elastic region 11 can be elasticised over the entire width of the first region 11. Alternatively, the first at least partly elastic region 11 can be elasticised on the transverse sides of the core 5 while keeping the area of the first region 11 that overlaps the core 5 substantially non-elasticised for avoiding undesirable deformation and contraction of the core 5. The area of the first region 11 that overlaps the core 5 may be made substantially non-elasticised by deactivating the elastic threads in that area, or by keeping that area free from elastic feature during manufacturing of the article.

The laminated web material of the front panel 3 further comprises a second at least partly elastic region 12 located next to the first at least partly elastic region 11 towards the waist edge 20 of the front panel 3. The second at least partly elastic region 12 may be referred to as an elastic belly region because it may, depending on the size of the second at least partly elastic region 12, extend over the belly of a user. The second at least partly elastic region 12 can be elasticised over the entire width of the second region 12. Alternatively, the second at least partly elastic region 12 can be elasticised on the transverse sides of the core 5 while keeping the area of the second region 12 that overlaps the core 5 substantially non-elasticised for avoiding undesirable deformation and contraction of the core 5.

The laminated web material of the front panel 3 has a third at least partly elastic region 13 extending primarily in the transverse direction X, being located adjacent the waist edge 20. The third at least partly elastic region 13 may consequently also be referred to as a waist elastic region.

The first at least partly elastic region 11 is distinct from the second at least partly elastic region 12 in terms of at least one structural elastic feature. For example, the structural elastic feature may be that an elasticised part 39 of the laminated web material of the first at least partly elastic region 11 may have a higher tensile stress at a given elongation in the transverse direction X than an elasticised part of the laminated web material of the second at least partly elastic region 12. The elasticised part 39 of any at least partly elastic region 11, 12 is a part of the laminated web material where the elastic is active and exerts a gathering-effect on the sheet material to which it is attached. With tensile stress at a given elongation is meant the tensile force per square are (N/m$^2$) with which an elasticised part 39 gathers the material it is located in.

The tensile stress of any elastic web material may for example be measured using a tensile tester, such as Instron Tester (Instron 5564, Instron corp.). For comparing tensile stress of an elasticised part of a laminated web material of the first at least partly elastic region 11 with the tensile stress of an elasticised part of the laminated web material of a second at least partly elastic region 12, at a given elongation in the transverse direction X, a first sample is cut from an elasticised part of the first elastic region into a first test piece having a length in the diapers transverse direction X and a width in the diapers longitudinal direction Y. Similarly a second sample is cut from an elasticised part of the second elastic region into a second test piece having equal size as the first sample. The end portions in the length direction of the sample are clamped on each side and the tensile test is carried out in the length direction of the sample. The cut pieces should be longer than the clamp distance and the elastic material should be present in the clamped area.

Based on a distance P between the clamps in which no external force is acting on the test piece and a distance Q between the clamps in which test piece is stretched to maximum, the test piece is stretched for one minute at a distance between the clamps represented by (P+Q)/2. After the minute the tensile stress between the clamps is measured as the contracting force per cross-section square area, wherein the cross-section square area of a sample is calculated as the width B of the sample times an average web material thickness of the sample. The results from the different tensile tests are compared.

Suitable width B is for example 20 mm but can be shorter if the first elastic region has a length in the longitudinal direction Y that is less than 20 mm. The width B then corresponds to the length of the first elastic region in the diapers longitudinal direction Y. Suitable length L of the test piece may for example be 350 mm.

The tensile test is performed, for each sample of elastic web material, under the same predetermined test conditions, such as crosshead speed and ambient conditions.

Higher tensile strength of the elastic web material the first elastic region can accomplished by having closer spacing between adjacent elastic threads than in the second elastic region, and/or by having elastic threads in the first elastic region with higher mass density than in the second elastic region, and/or by having elastic threads in the first elastic region applied with a higher level of elongation than in the second elastic region.

Alternatively, the structural elastic feature may be the spacing between neighbouring elastic threads. For example, the spacing between neighbouring elastic threads of the first at least partly elastic region 11 may be smaller than the spacing between neighbouring elastic threads of the second at least partly elastic region 12. This would typically result in higher tensile stress at the first at least partly elastic region 11 for any given elongation.

Still more alternatively, the structural elastic feature may be the mass density of the elastic threads, or the level of elongation of the elastic threads with the front panel 3 in a flat and un-gathered state.

The back panel 4, as schematically illustrated in FIGS. 1a, 1b and 2, comprises a waist edge 25, a pair of leg edges 27a, 27b and a pair of side edges 10a, 10b. The back panel 4 may have a shape composed of a substantially rectangular shaped main section 28 intended to be located towards a waist of a user and a substantially trapezoid shaped buttocks-covering section 29 intended to be located towards a crotch of a user. A certain level of variations in said schematic geometry is of course possible. For example, the side edges of said sections 28, 29 may for example be non-linear, the corners may be more rounded, the total length of the buttocks-covering section 29 in the transverse direction X may be smaller than the total length of the main section 28 in the transverse direction X, etc. A substantially trapezoid shaped buttocks-covering section 29 provides improved fit and comfort to a user, as well as improved underwear-like visual appearance.

In the example embodiment of FIGS. 1a to 2 the main section 28 of the back panel 4 has shape that substantially corresponds to the rectangular-shaped front panel 3. In other words, the length of the main section 28 of the back panel 4 in the longitudinal direction Y is substantially equal to the length of the rectangular-shaped front panel 3 in the longitudinal direction Y, and the length of the main section 28 of the back panel 4 in the transverse direction X is substantially equal to the length of the rectangular-shaped front panel 3 in the transverse direction X.

According to a further example embodiment, the length of the main section 28 of the back panel 4 in the longitudinal direction Y may be substantially equal to the length of the side seam 6a, 6b in the longitudinal direction Y.

The first at least partly elastic region 11 of the front panel 3 may comprise a plurality of elastic threads arranged parallel at substantially equally spaced intervals of for example about 2 to 8 millimetres and may for example comprise about 4 to 6 elastic threads. Each of the elastic threads may have substantially equal mass density, which for example may lie in the range 600 to 1200 decitex, specifically in the range of 750 to 1000 decitex.

The second at least partly elastic region 12 of the front panel 3 typically corresponds to the belly portion of the absorbent article 1 and may comprise a plurality of elastic threads arranged parallel at substantially equally spaced intervals of for example about 5 to 13 millimetres and may for example comprise about 9 to 27 elastic threads. Each of the elastic threads may have substantially equal mass density, which for example may lie in the range 350 to 900 decitex, specifically in the range of 500 to 700 decitex. Having relatively large intervals between neighbouring elastic threads in a belly portion in relation to the lower area of the front panel 3 enables a large and comfortable belly portion.

The third at least partly elastic region 13 of the front panel 3 may comprise a plurality of elastic threads arranged in parallel at substantially equally spaced intervals of for example about 2 to 8 millimetres and for example comprise about 4 to 6 elastic threads. Each of the elastic threads may have substantially equal mass density, which for example may lie in the range 600 to 1200 decitex, specifically in the range of 750 to 1000 decitex.

An upper region 31 of the back panel 4 may comprise a plurality of elastic threads arranged parallel at substantially equally spaced intervals of for example about 2 to 8 millimetres and may for example comprise about 4 to 6 elastic threads. Each of the elastic threads may have substantially equal mass density, which for example may lie in the range 600 to 1200 decitex, specifically in the range of 750 to 1000 decitex.

A middle region 32 of the back panel 4 may comprise a plurality of elastic threads arranged parallel at substantially equally spaced intervals of for example about 5 to 13 millimetres and may for example comprise about 7 to 18 elastic threads. Each of the elastic threads may have substantially equal mass density, which for example may lie in the range 350 to 900 decitex, specifically in the range of 500 to 700 decitex.

A lower region 33 of the back panel 4 extending over the buttocks of the user may comprise a plurality of elastic threads arranged parallel at substantially equally spaced intervals of for example about 10 to 30 millimetres and may for example comprise about 3 to 9 elastic threads. Each of the elastic threads may have substantially equal mass density in the range 350 to 900 decitex, specifically in the range of 500 to 700 decitex.

The uniform characteristic of the elastic threads in a certain elastic region (e.g. the first at least partly elastic region 11 of the front panel 3 may have equal intervals between neighbouring threads, thereby distinguishing from a neighbouring elastic region (e.g. the first at least partly elastic region 12 of the front panel 3 having a different interval between neighbouring elastic threads. Alternatively, the uniform characteristic the elastic threads in a certain at least partly elastic region may be having is equal mass density, thereby distinguishing the region from a neighbouring at least partly elastic region having a different mass density of the elastic threads. According to still a further alternative, the uniform characteristic of the elastic threads in a certain at least partly elastic region may be a specific level of elastic stretching of the elastic threads during manufacturing, thereby distinguishing the region from a neighbouring at least partly elastic region having a different specific level of elastic stretching of the elastic threads during manufacturing.

Since it may be advantageous to have the side seams 6a, 6b free from adhesive the continuous elastic threads will in the area of the side seam 6a, 6b during manufacturing of the absorbent article 1 snap back upon the cutting operation required for splitting the continuous material band into individual absorbent articles. Therefore a narrow longitudinal strip 24a, 24b of material is illustrated having no elastic threads attached thereto in FIG. 2. Therefore, the first, second and third elastic regions 11, 12, 13 do not necessarily extend out to the side edges 9a, 9b of the front panel 3, as shown in FIG. 2. The same may be done for the back panel 4.

The article 1 has an absorbent insert 2 located mainly in a crotch portion of the absorbent article 1 and being connected to the front and back panels 3, 4. The insert 2 comprises an absorbent core 5 with longitudinal core edges 14, a front core edge 15 and a back core edge 16. The longitudinal core edges 14, the front core edge 15 and the back core edge 16 jointly define the outer perimeter of the core 5. The front and back core edges 15, 16 refer to the edges of the core 5 that extend primarily or only in the transverse direction X. The longitudinal core edges 14 extend between the front and back core edges 15, 16 generally in the longitudinal direction Y, but the longitudinal core edges 14 may locally have other orientations, depending on the design of the core.

The core 5 has a front segment 17 with a length L2 in the longitudinal direction Y which is 30% of the total length L5 of core 5 in the longitudinal direction Y and extending from the front core edge 15 towards the back of the core 5, a back segment 18 with a length L3 in the longitudinal direction Y which is 30% of the total length L5 of core 5 in the longitudinal direction Y and extending from a back core edge 16 towards to the front of the core 5, and a middle segment 19 with a length L4 in the longitudinal direction Y which is 40% of the total length L5 of core 5 in the longitudinal direction Y and being located between the front and back segments 17, 18. The core 5 consequently comprises three segments 17, 18, 19 defined by two parallel and spaced apart transversally extending lines, each crossing the core 5.

The core 5 has a wide portion 22 in the front segment 17. The wide portion 22 has a width W1 in the transverse direction X that is at least 1.1 times greater than the maximal width W2 in the transverse direction X of the core 5 in the back segment 18. In other words, all parts of the front segment 17 that has a transverse width W1 that is 1.1 times greater or more than the maximal transverse width W2 of the core 5 in the back segment 18 defines one or more wide portions 22. The transverse width W1 may this vary over a length L1 of the wide portion 22 and is not necessarily constant. In fact, the transverse width W1 tend to vary over the length L1 of the wide portion 22 as soon as the front segment 17 has a more rounded and less rectangular outer shape. The length L1 is defined as the length of the wide portion 22 where the width W1 is 1.1 times greater, or more, than the maximal transverse width W2 of the core 5 in the back segment 18. In FIG. 2 the limit width that is exactly 1.1 times greater than the maximal transverse width W2 of the core 5 in the back segment 18 is marked with W3. The longitudinal length L1 of the wide portion 22 is consequently in FIG. 2 defined by the intersection of the longitudinal core edges 14 with longitudinal lines defined by width W3 and centred around a longitudinal centre line of the absorbent article.

The wide portion 22 may extend down into the middle segment 19. The wide portion 22 typically extends over less than 50%, specifically less than 35%, and more specifically less than 20% of the middle segment 19.

The core 5 typically comprises a single wide portion 22 located mainly over the front segment 17.

The absorbent core 5 comprises pulp fibres and superabsorbent particles. The area of the absorbent insert 2 located outside of the absorbent core 5 is substantially free from pulp fibres and superabsorbent particles, except possibly for a small level of dislocation of pulp and/or superabsorbent particles during manufacturing and transportation. The perimeter of the core 5 is consequently easily detectable, and the transverse width of the core 5 can therefore easily be determined over the entire longitudinal length of the core 5.

The elasticised part 39 of the laminated web material of the first at least partly elastic region 11 meet the core 5 in said wide portion 22 of the core 5. The meeting takes place at an outer perimeter of the core, i.e. at an outer edge of the core. Since the first at least partly elastic region 11 extends primarily in the transverse direction the meeting between the elasticised part 39 of the laminated web material of the first at least partly elastic region 11 and the wide portion 22 of the core 5 will occur at a longitudinal core edge 14.

That the elasticised part 39 of the laminated web material of the first at least partly elastic region 11, or an inner imaginary extension 23 of the elasticised part 39 of the laminated web material of the first at least partly elastic region 11, meet the core 5 in said wide portion 22 of the core 5 means that the elasticised part 39, intersect an edge of the core 5 in said wide portion 22 of the core 5 or adjoin the core 5 in the wide portion of the core 5.

The core 5 may also have side elastic elements 30 extending along the longitudinal core edges 14. The side elastic elements 30 are arranged to provide a side gathering effect along the transverse sides of the front segment of the core. A gathering effect means that the absorbent core 5 within the region of the side elastic element 30 may contract in the direction of extension of the side elastic elements 30. This contraction effect of the material of the absorbent article along the transverse sides of a front segment will assist forming of the internal pocket in the absorbent article, and thus generating a more comfortable and leakage secure absorbent article.

Each elongated side elastic element 30 may include one or more individual elastic threads, such as for example two, three or four elastic threads placed parallel to each other and with a gap between each other. The length of the side elastic element 30 in the longitudinal direction Y may be in the range of 4-20 centimetres, specifically 5-15 centimetres, and more specifically 5-10 centimetres.

The side elastic element 30 may extend from the back or middle segment 18, 19 towards the front core edge 15. The longitudinal distance from a front core edge 15 to the edge of the side elastic element 30 may be less than 30 millimetres, and specifically less than 15 millimetres. The side elastic elements 30 may even extend beyond the front core edge 15 towards the front waist edge 20 of the absorbent article 1. The side elastic elements 30 may be attached to a chassis of the absorbent article, and/or to transverse sides of the insert 2, and/or to the transverse sides of the absorbent core 5.

As illustrated in FIG. 2, each elongated side elastic element 30 may be designed to extend backwards in the longitudinal direction y along the transverse sides of the absorbent core 5 to also form leg elastic members along the periphery of the leg-openings in a crotch section of the article 1. This arrangement thus enables combined use of one-piece longitudinally oriented elastic members 30 on each transverse side of the absorbent core 5, such that the need for mounting of separate leg elastic feature and internal pocket gather elastics can be avoided to save cost and simplify manufacturing. Alternatively, the side elastic elements 30 may extend mainly along the front segment 17 of the core only, and other side elastic elements may be used for accomplishing the desired gathering effect along the periphery of the leg-openings in a crotch section of the article.

Figure 3:
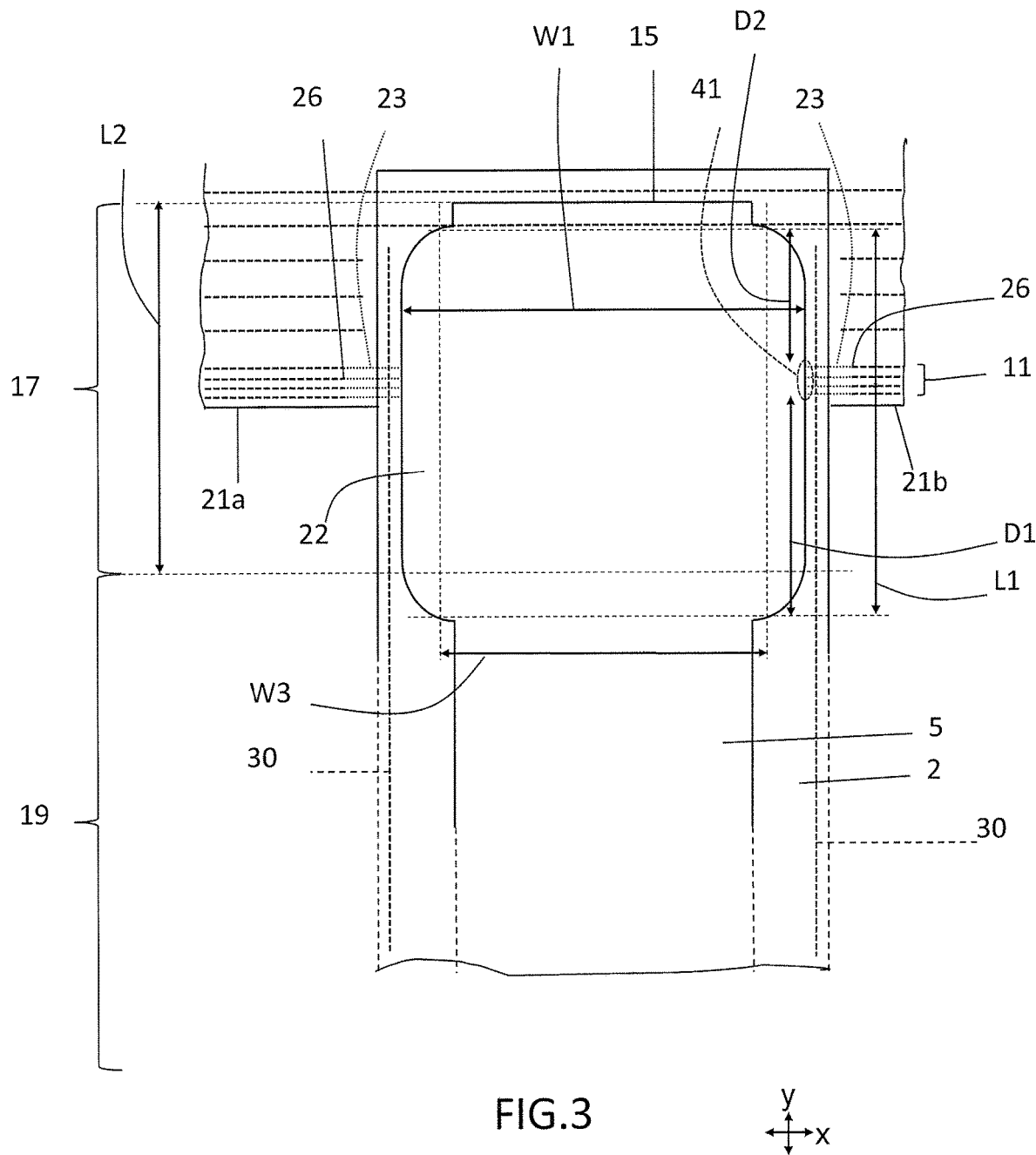
FIG. 3 shows a detailed view of an alternative embodiment of FIG. 2.

FIG. 3 shows a detailed view of an alternative embodiment of the article 1 of FIG. 2. In FIG. 3 the elasticised part 39 of the laminated web material of the first at least partly elastic region 11 extends from the outer end adjacent the side edges 9a, 9b of the front panel 3 to an inner end 26 located spaced apart from the core 5. The inner imaginary extension 23 of an elasticised part 39 of the laminated web material of the first at least partly elastic region 11 extends linearly from the inner end 26 of a linear portion of an elasticised part 39 of the laminated web material of the first at least partly elastic region 11 to meet the core 5 in the wide portion 22.

With reference to FIGS. 2 and 3, the wide portion of the core 5 may extend a first longitudinal distance D1 corresponding to at least 20% of the length of the front segment 17 of the core 5 below a position 41 where either the elasticised part 39 of the laminated web material of the first at least partly elastic region 11, or the inner imaginary extension 23 of the elasticised part 39 of the laminated web material of the first at least partly elastic region 11, meets the longitudinal core edge. Furthermore, the wide portion of the core 5 may extend a second longitudinal distance D2 corresponding to at least 20% of the length of the front segment 17 of the core 5 above the position 41.

Figure 4:
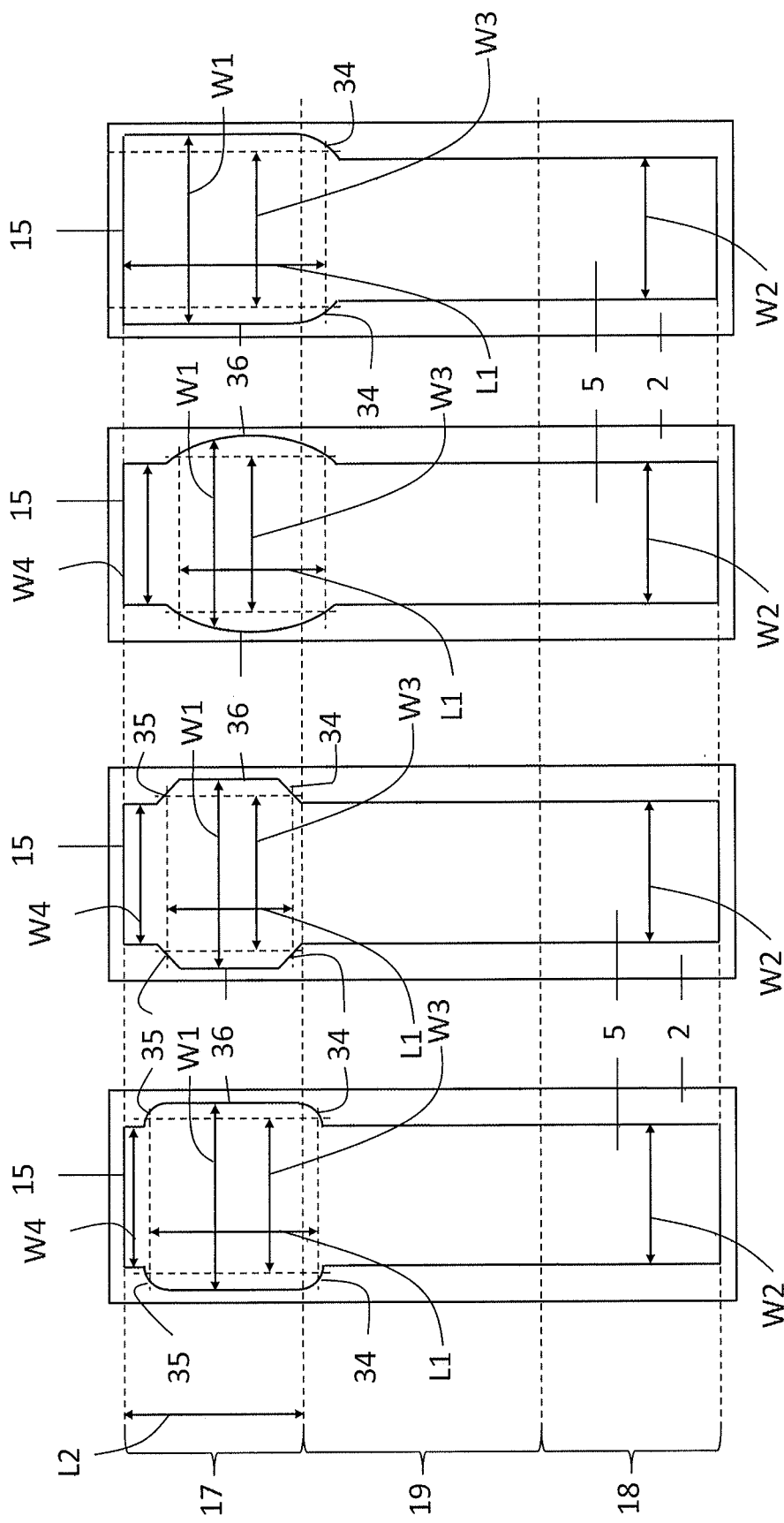
FIGS. 4a-4d shows examples of core shapes according to the disclosure.

FIGS. 4a-4d shows alternative embodiments of the wide portion 22 in the front segment 17 of the core 5. FIG. 4a shows a wide portion 22 having rounded edges forming lower transitions 34 of the wide portion 22 and the remainder of the core 5 in a bottom part of the wide portion 22. A middle part 36 of the wide portion 22 extends between the lower transitions 34 and upper transitions 35 and is essentially straight in a longitudinal direction Y before rounded edges form upper transitions 35 back to a width W4 adjacent the front core edge 15 which is narrower than the width W1 of the wide portion 22. The width W3 indicates where the width of the wide portion 22 is at least 1.1 times the maximal transverse width W2 of the core 5 in the back segment 18.

FIG. 4b shows a wide portion 22 with straight lines forming the lower transitions 34 of the wide portion 22 and the remainder of the core 5 in a bottom part of the wide portion 22. A middle part 36 of the wide portion 22 between the lower transitions 34 and upper transitions 35 is essentially straight in a longitudinal direction Y before straight lines form upper transitions 35 back to a width W4 adjacent the front core edge 15 which is narrower than the width W1 of the wide portion 22. The width W3 indicates where the width of the wide portion 22 is at least 1.1 times the maximal transverse width W2 of the core 5 in the back segment 18.

FIG. 4c shows a wide portion 22 having a curved shape. The wide portion 22 transitions directly from the remainder of the core 5 to a middle part 36 having a curved shape. The curved shape is for instance part of a circle or an oval. At least the widest part of the curved shape has a width of at least 1.1 times greater than the maximal width W2 in the transverse direction X of the core 5 in the back segment 18. The wide portion 22 transitions directly to a width W4 adjacent the front core edge 15 which is narrower than the width W1 of the wide portion 22.

In FIGS. 4a-4c the width W4 of the core 5 adjacent the front core edge 15 in the transverse direction X may be smaller than the width of the core 5 in the transverse direction X in the rest of the front segment 17 of the core 5. The width of the core 5 adjacent the front core edge 15 in the transverse direction X may be equal to the width of at least part of the core 5 in the back segment 18 of the core 5 in the transverse direction X.

FIG. 4d shows a wide portion 22 of the core 5 with rounded edges forming the lower transition 34 between the wide portion 22 and the remainder of the core 5 in the bottom part of the wide portion 22. The middle part 36 of the wide portion 22 is essentially straight in a longitudinal direction Y. In this example there are no upper transitions 35 to a narrower width, instead the wide portion 22 maintains its width to the front core edge 15.

The length L1 of the wide portion is measured from where the width of the wide portion is at least 1.1 times greater than the maximal width W2 of the back segment 18. As can be seen from the figures the wide portion 22 can have a greater or a smaller longitudinal length L1 than the length L2 of the front segment 17. Additionally, the lower transitions 34 and the upper transitions 35 do not have to have the same shape. Further, the shape of the transitions 34, 35 are mere illustrations and can take other shapes than the ones shown.

The wide portion 22 has a length L1 in the longitudinal direction Y in the range of 30-200 millimetres, specifically 40-180 millimetres, and more specifically 50-160 millimetres. The wide portion 22 has a length L1 in the longitudinal direction Y in the range of 20-130%, specifically 25-120%, and more specifically 30-100% of the length L2 of the front segment 17 of the core 5.

Figure 5:
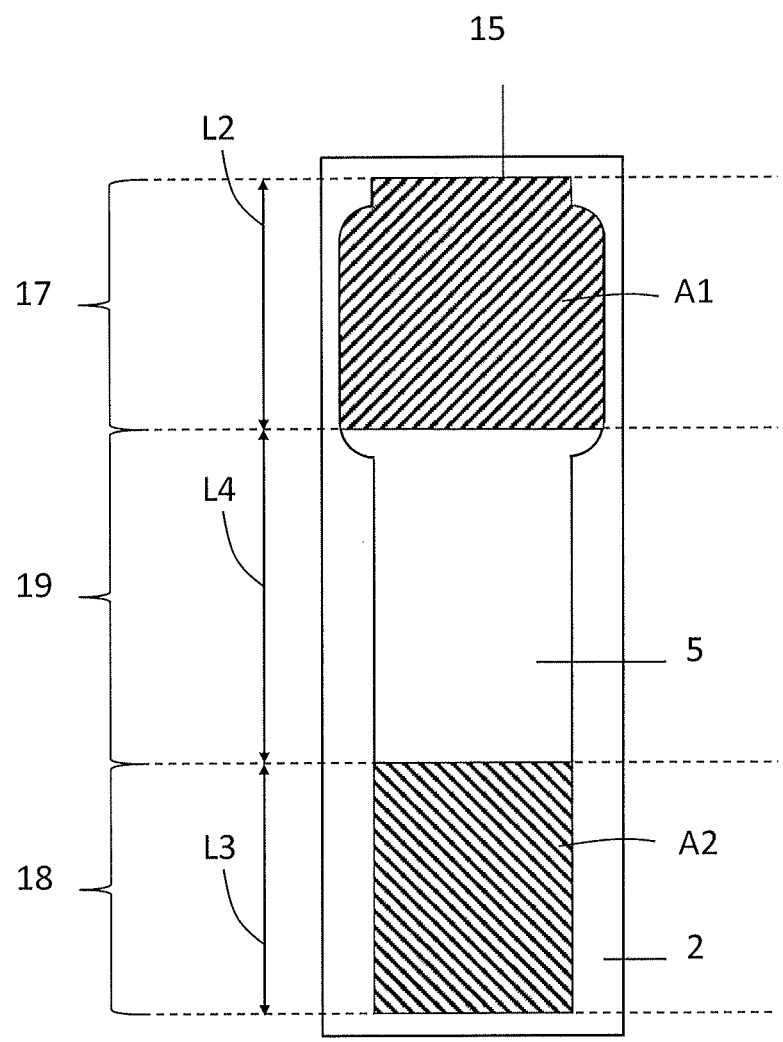
FIG. 5 illustrates the surface area of the front and back segment of an example embodiment of a core.

As schematically illustrated in FIG. 5, the front segment 17 of the core 5 has an area A1 which is at least 1.1 times greater, specifically at least 1.2 times greater, and more specifically at least 1.3 times greater than an area A2 of the back segment 18 of the core 5. One advantage with having a larger area A1 of the front segment 17 of the core 5 than the area A2 of the back segment 18 of the core 5 is that the core 5 will have a greater area where the likelihood of urine discharge is the greatest. This further increases the likelihood that the urine discharge will be absorbed by the core 5 and will not fall outside of the core 5. The area herein refers to the surface area of the core on the side intended to face the user.

Figure 6:
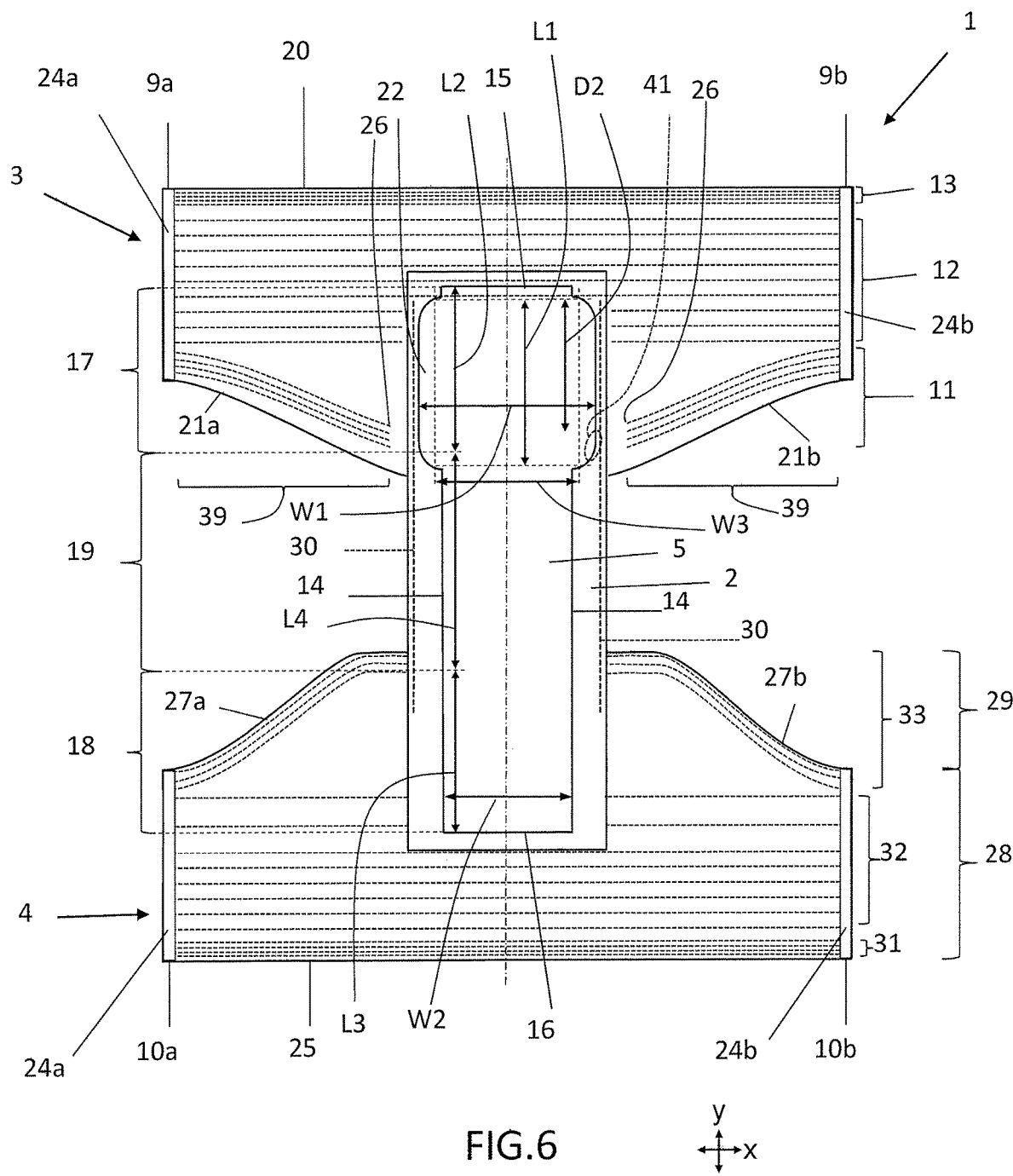
FIG. 6 shows a perspective view of an alternative embodiment of an absorbent article according to the disclosure.

FIG. 6 shows an alternative embodiment to the articles 1 in FIGS. 1a and 1b. In FIG. 6 both the front panel 3 and the back panel 4 have a shape composed of a substantially rectangular shaped main section 37 intended to be located towards a waist of a user and a substantially trapezoid shaped section 38 intended to be located towards a crotch of a user. A certain level of variations in said schematic geometry is of course possible. In this embodiment the elasticised region of the first at least partly elastic region 11 comprises curved portions. In this embodiment the inner imaginary extension of the elasticised part 39 of the laminated web material of the first at least partly elastic region 11 may extend tangentially from the inner end 26 of a curved portion of an elasticised part 39 of the laminated web material of the first at least partly elastic region 11 to meet the core 5 when the inner end 26 of the elasticised part 39 is located spaced apart from the core 5. Due to the position of the elasticised part 39 at a lowermost end of the wide portion of the core 5 in FIG. 6, D1 is not shown in this figure. Only D2 is labeled in the drawing.

All measurements are made with the product cut open at the side seals and held flat in a state in which the absorbent article 1 has been extended in both the longitudinal and transverse direction to such an extent that all the elastics contained therein are extended to such an extent that they no longer gather any part of the product, but the entire absorbent article 1 is completely flat and in an un-gathered state. The article 1 is extended only to such an extent that this flat condition is reached.

By "absorbent article" is meant an article that absorbs or is adapted to absorb bodily fluids, such as urine and/or blood.

The nonwoven material layers or webs of the present disclosure forming the front and back panels may for example be selected from, for example, of spunbond, air laid, wet laid, carded, electro spunned or meltblown nonwovens. The nonwoven material may be bonded by multiple techniques, e.g. by needling, hydroentangling, or heat bonding.

The nonwoven material of the disclosed products is a mixture of natural and synthetic materials. Natural fibres are for instance cellulosic fibres or fibres from regenerated cellulose.

The term "elastic thread" is intended to mean an elastic strand or elastic thread which is made of elastic material, such as e.g. natural or synthetic rubber, thermoplastic elastomers, such as thermoplastic polyurethane or styrene block co-polymers or elastane, also referred as to spandex (polyurethane-polyurea copolymer). The threads may be of the elastane type that is available under the trade name "LYCRA", but any suitable elastic thread may be used. The threads may have a linear mass density, dtex, of about 80-1200 dtex.

The elastic threads are elongated during the production process from about 50 to about 300% of the initial, non-tensioned original length, for example, may preferably be 100-250% or may preferably be 150-220% of the initial, non-tensioned original length. The elastic threads may, for example preferably be of a type that are able to tolerate an elongation of at least about 200% without breaking, so that they can be safely used in the production process without risk for breaking.

The laminated web material of the front panel and/or back panel 3, 4 may alternatively, or in combination with elastic threads, be elasticised by means of elastic film material laminated between sheets of the front and/or back panels 3, 4. Using an elastic film material may be advantageous because it may enable the resulting elasticised laminated web material to be elastic in both the longitudinal and transverse directions Y, X.

Further information with respect to material about the elastic web material is disclosed in WO2014098683 A1, which is referred to in its entirety.

The absorbent core may comprise any conventional material suitable for absorbing discharged bodily wastes, such as cellulosic fluff pulp, tissue layers, highly absorbent polymers (super absorbents), absorbent foam materials including hydrogel-foam material, absorbent nonwoven materials or the like.

The absorbent core may have a liquid permeable topsheet placed on the side intended to face the skin of a user, and a liquid impermeable backsheet placed on the side of the absorbent core intended to face the garment of a user. Generally, the liquid permeable topsheet comprises or consist of a nonwoven material. The topsheet material may further be composed of tow fibres, porous foams, apertured plastic films etc. As mentioned above, the materials suited as topsheet materials should be soft and non-irritating to the skin and be readily penetrated by body fluid, e.g. urine or menstrual fluid, and display low rewetting properties.

The liquid impermeable backsheet may consist of a thin plastic film, e. g. a polyethylene or polypropylene film, a nonwoven material coated with a liquid impervious material, a hydrophobic nonwoven material which resists liquid penetration or laminates of plastic films and nonwoven materials. The backsheet material may be breathable so as to allow vapour to escape from the absorbent core, while still preventing liquids from passing through the backsheet material.

The topsheet and backsheet may be connected to each other for example by adhesive bonding, gluing or welding by heat or ultrasonic. The topsheet and/or the backsheet may further be attached to the absorbent core by any method known in the art, such as adhesive, heat-bonding etc.

The topsheet and backsheet of the absorbent core 5 may extend outwardly beyond the area of the absorbent core 5, thereby defining an absorbent insert 2 comprising an absorbent core 5. The maximal width of the absorbent core 5 is typically about 120 to 200 mm in transverse direction X, and the maximal length L5 of the absorbent core 5 is typically and 400 to 600 mm in longitudinal direction Y.

The absorbent core 5 may overlap the front panel 3 with a longitudinal length of about 50-100 mm. Moreover, the absorbent core 5 may overlap the back panel 4 with a longitudinal length of about 200-250 mm; alternatively, the absorbent core 5 may overlap the main section 28 of the back panel 4 with a longitudinal length of about 30-70 mm.

Reference signs mentioned in the claims should not be seen as limiting the extent of the matter protected by the claims, and their sole function is to make claims easier to understand.

As will be realised, the disclosure is capable of modification in various obvious respects, all without departing from the scope of the appended claims. Accordingly, the drawings and the description thereto are to be regarded as illustrative in nature, and not restrictive. It should be understood that the present absorbent articles and its components and methods are not intended to be limited to the particular forms disclosed. Rather, they are intended to include all modifications, equivalents, and alternatives falling within the scope of the claims. They are further intended to include embodiments that may be formed by combining features from the disclosed embodiments, and variants thereof.

FEATURES

1. Absorbent article
2. Absorbent insert
3. Front panel
4. Back panel
5. Absorbent core
6. Side seams (a, b)
7. Waist opening
8. Leg opening
9. Front panel side edges (a, b)
10. Back panel side edges (a, b)
11. First at least partly elastic region
12. Second at least partly elastic region
13. Third at least partly elastic region
14. Longitudinal core edges
15. Front core edge
16. Back core edge
17. Front segment
18. Back segment
19. Middle segment
20. Front panel waist edge
21. Front panel leg edges (a, b)
22. Wide portion
23. Imaginary extension
24. Longitudinal strip (a, b)
25. Back panel waist edge
26. Inner end
27. Back panel leg edges (a, b)
28. Back panel main section
29. Back panel trapezoid section
30. Side elastic elements
31. Upper region
32. Middle region
33. Lower region
34. Lower transition
35. Upper transition
36. Middle part
37. Front panel main section
38. Front panel trapezoid section
39. Elasticised part
A1. Area of front segment of the core
A2. Area of back segment of the core
W1. Width of wide portion
W2. Maximal width of core in back segment
W3. Limit width defining wide portion
L1. Length of wide portion
L2. Length of front segment
L3. Length of back segment
L4. Length of middle segment
L5. Total length of core

The invention claimed is:
1. A disposable pant-type absorbent article having a longitudinal direction (Y) and a transverse direction (X), said disposable pant-type absorbent article being adapted for a male user and comprising:

a front panel made of laminated web material and having a front waist edge, a pair of front leg edges and a pair of front side edges,
a back panel having a back waist edge, a pair of back leg edges, a pair of back side edges, and
an absorbent insert located mainly in a crotch portion of the absorbent article and being connected to the front panel and the back panel and having an absorbent core with longitudinal core edges, a front core edge, and a back core edge,
wherein the core has a front segment with a front segment length in the longitudinal direction (Y) which is 30% of the total length of the core in the longitudinal direction (Y) and extending from a front core edge, a back segment with a back segment length in the longitudinal direction (Y) which is 30% of the total length of the core in the longitudinal direction (Y) and extending from the back core edge, and a middle segment with a middle segment length (L4) in the longitudinal direction (Y) which is 40% of the total length of the core in the longitudinal direction (Y) and being located between the front segment and the back segment,
wherein the absorbent core has a wide portion in the front segment, which wide portion has a wide portion width in the transverse direction (X) that is at least 1.1 times greater than a back maximal width in the transverse direction (X) of the core in the back segment,
wherein the laminated web material of the front panel has a first at least partly elastic region extending primarily in the transverse direction and being located adjacent the leg edges of the front panel, and a second at least partly elastic region extending primarily in the transverse direction and being located next to the first at least partly elastic region and closer to the front waist edge of the front panel,
wherein the first at least partly elastic region is distinct from the second at least partly elastic region in terms of an at least one structural elastic feature making the first at least partly elastic region distinct from the second at least partly elastic region,
wherein either (a) an elasticised part of the laminated web material of the first at least partly elastic region, or (b) an inner imaginary extension of the elasticised part of the laminated web material of the first at least partly elastic region, meets a longitudinal core edge of said wide portion of the front segment of the core,
wherein the wide portion extends a first longitudinal distance corresponding to at least 20% of the length of the front segment of the core below a position where either (a) the elasticised part of the laminated web material of the first at least partly elastic region, or (b) the inner imaginary extension of the elasticised part of the laminated web material of the first at least partly elastic region, meets the longitudinal core edge, and
wherein the wide portion extends a second longitudinal distance corresponding to at least 20% of the length of the front segment of the core above the position where either (a) the elasticised part of the laminated web material of the first at least partly elastic region, or (b) the inner imaginary extension of the elasticised part of the laminated web material of the first at least partly elastic region, meets the longitudinal core edge.

2. The disposable pant-type absorbent article according to claim 1, wherein the at least one structural elastic feature making the first at least partly elastic region distinct from the second at least partly elastic region comprises at least one of the following:

the elasticised part of the laminated web material of the first at least partly elastic region has a higher tensile stress at a given elongation in the transverse direction (X) than an elasticised part of the laminated web material of the second at least partly elastic region;

the spacing between neighbouring elastic threads;

the mass density of the elastic threads; or the level of elongation of the elastic threads with the front panel in a flat and un-gathered state.

3. The disposable pant-type absorbent article according to claim 1, wherein the front segment of the core has an area which is at least 1.1 times greater than an area of the back segment of the core.

4. The disposable pant-type absorbent article according to claim 1, wherein the wide portion in the front segment has a length in the longitudinal direction (Y) in the range of 30-200 millimetres.

5. The disposable pant-type absorbent article according to claim 1, wherein the wide portion has a length in the longitudinal direction (Y) in the range of 20-130% of the length of the front segment of the core.

6. The disposable pant-type absorbent article according to claim 1, wherein the wide portion of the core has the wide portion width in the transverse direction (X) that is at least 1.2 times greater than the back portion maximal width in the transverse direction of the core in the back segment.

7. The disposable pant-type absorbent article according to claim 1, wherein the elasticised part of the laminated web material of the first at least partly elastic region extends from an outer end adjacent one of the pair of side edges of the front panel to an inner end located spaced apart from the core, and the inner imaginary extension of the elasticised part of the laminated web material of the first at least partly elastic region extends linearly from the inner end of a linear portion of the elasticised part of the laminated web material of the first at least partly elastic region, or extends tangentially from an inner end of a curved portion of an elasticised part of the laminated web material of the first at least partly elastic region.

8. The disposable pant-type absorbent article according to claim 1, wherein a width of the core adjacent the front core edge, in the transverse direction (X), is constant over a longitudinal extent of the core in the longitudinal direction (Y), and is smaller than the width of the core in the transverse direction (X) in the rest of the front segment of the core.

9. The disposable pant-type absorbent article according to claim 1, wherein a width of the core adjacent the front core edge in the transverse direction (X) is equal to a width of at least part of the core in the back segment of the core in the transverse direction (X).

10. The disposable pant-type absorbent article according to claim 1, wherein an elasticised part of the laminated web material of the second at least partly elastic region extends over an area of the front segment of the absorbent core, which area of the front segment extends from the front core edge in the longitudinal direction (Y) by less than or equal to 30 mm, such that the front core edge is configured to be pressed towards a user during use of the absorbent article.

11. The disposable pant-type absorbent article according to claim 1, wherein the front segment is configured for receiving the genitals of a male user, wherein elasticised parts of the laminated web material of the first at least partly elastic region extends on transverse sides of the front segment but not completely over the front segment for enabling the absorbent core in the front segment to bulge outwardly during use of the article, wherein the absorbent article further comprises at least one elongated side elastic element attached in a substantially longitudinal direction on each transverse side of the front segment for providing a side gathering effect along the transverse sides of the front segment, such that the absorbent core within the front segment, under the influence of the side elastic elements is adapted to bulge outwardly during use of the article to form an internal pocket for receiving the genitals of a male user.

12. The disposable pant-type absorbent article according to claim 1, wherein the elasticised part of the laminated web material of the first at least partly elastic region, and/or an elasticised part of the laminated web material of the second at least partly elastic region, end(s) before the longitudinal core edges.

13. The disposable pant-type absorbent article according to claim 1, wherein the elasticised part of the laminated web material of the first at least partly elastic region overlaps the longitudinal core edges of the absorbent core.

14. The disposable pant-type absorbent article according to claim 1, wherein the front panel and the back panel are made of individual parts that are mutually interconnected by means of the absorbent insert, and wherein the front panel has a length in the longitudinal direction (Y) of between 110-400 mm.

15. The disposable pant-type absorbent article according to claim 1, wherein the first at least partly elastic region has a length in the longitudinal direction (Y) of 5-30 mm.

16. The disposable pant-type absorbent article according to claim 1, wherein the ratio of a fluid absorbent capacity of a front half length of the absorbent core to a fluid absorbent capacity of a back half length of the absorbent core is at least 55 to 45.

17. The disposable pant-type absorbent article according to claim 1, wherein a maximal width of the absorbent core is between 120-200 mm in the transverse direction (X) and wherein a minimal width of the absorbent core is 60 mm in the transverse direction (X).

18. The disposable pant-type absorbent article according to claim 1, wherein the laminated web material of the front panel has a third at least partly elastic region extending primarily in the transverse direction (X), being located adjacent the front waist edge.

19. The disposable pant-type absorbent article according to claim 1, wherein the absorbent core comprises pulp fibres and superabsorbent particles.

20. The disposable pant-type absorbent article according to claim 1, wherein an area of the absorbent insert located outside of the absorbent core is substantially free from pulp fibres and superabsorbent particles.

21. The disposable pant-type absorbent article according to claim 1, wherein the core is free of overlap, along the transverse direction (X), with the elasticised part of the laminated web material of the first at least partly elastic region.

22. A method for manufacturing a disposable pant-type absorbent article having a longitudinal direction (Y) and a transverse direction (X), said disposable pant-type absorbent article being adapted for a male user and comprising:

a front panel made of laminated web material and having a front waist edge, a pair of front leg edges and a pair of front side edges, a back panel having a back waist edge, a pair of back leg edges, and a pair of back side edges, an absorbent insert located mainly in a crotch portion of the absorbent article and being connected to the front panel and the back panel and having an absorbent core, wherein the absorbent core has a front segment with a front segment length in the longitudinal direction (Y) which is one-third of the total length of the core in the longitudinal direction (Y) and extending from a front core edge, a back segment with a back segment length in the longitudinal direction (Y) which is one-third of the total length of the absorbent core in the longitudinal direction (Y) and extending from a back core edge, and a middle segment with a middle segment length in the longitudinal direction (Y) which is one-third of the total length of the core in the longitudinal direction (Y) and being located between the front segment and the back segment, wherein the method comprises:
providing the core with a wide portion in the front segment, which wide portion has a wide portion width in the transverse direction (X) that is at least 1.1 times greater than a back maximal width in the transverse direction (X) of the core in the back segment, providing the laminated web material of the front panel with a first at least partly elastic region extending primarily in the transverse direction (X) and being located adjacent both the leg edges of the front panel, providing the laminated web material of the front panel with a second at least partly elastic region extending primarily in the transverse direction (X) and being located next to the first elastic region and closer to the front waist edge of the front panel, providing the first at least partly elastic region with at least one structural elastic feature distinguishing the first at least partly elastic region from the second at least partly elastic region in terms of an at least one structural elastic feature making the first at least partially elastic region distinct from the second at least partially elastic region, and arranging either (a) an elasticised part of the laminated web material of the first at least partly elastic region, or (b) an inner imaginary extension of the elasticised part of the laminated web material of the first at least partly elastic region, such that the elasticized part or the inner imaginary extension meets a longitudinal core edge of said wide portion of the front segment, wherein the wide portion extends a first longitudinal distance corresponding to at least 20% of the length of the front segment of the core below a position where either (a) the elasticised part of the laminated web material of the first at least partly elastic region, or (b) the inner imaginary extension of the elasticised part of the laminated web material of the first at least partly elastic region, meets the longitudinal core edge, and wherein the wide portion extends a second longitudinal distance corresponding to at least 20% of the length of the front segment of the core above the position where either (a) the elasticised part of the laminated web material of the first at least partly elastic region, or (b) the inner imaginary extension of the elasticised part of the laminated web material of the first at least partly elastic region, meets the longitudinal core edge.

23. The method according to claim 22, wherein a width of the core adjacent the front core edge, in the transverse direction (X), is constant over a longitudinal extent of the core in the longitudinal direction (Y), and is smaller than the width of the core in the transverse direction (X) in the rest of the front segment of the core.

24. The method according to claim 22, wherein the core is free of overlap, along the transverse direction (X), with the elasticised part of the laminated web material of the first at least partly elastic region.

* * * * *